United States Patent [19]

Kohlhaupt et al.

[11] Patent Number: 5,075,458

[45] Date of Patent: Dec. 24, 1991

[54] PURIFICATION OF INDIGO

[75] Inventors: Reinhold Kohlhaupt, Frankenthal; Manfred Gaeng, Bobenheim-Roxheim; Lothar Haas, Dannstadt-Schauernheim; Guenter Engelhardt, Mannheim; Walter Bieg, Gruenstadt; Matthias Fankhaenel, Mannheim, all of Fed. Rep. of Germany

[73] Assignee: BASF Aktiengesellschaft, Ludwigshafen, Fed. Rep. of Germany

[21] Appl. No.: 684,873

[22] Filed: Apr. 15, 1991

[51] Int. Cl.$^5$ .............................................. C07D 403/04
[52] U.S. Cl. ..................................................... 548/457
[58] Field of Search ......................................... 548/457

[56] References Cited

U.S. PATENT DOCUMENTS 4,966,979  10/1990  Takaki et al. ...................... 548/457

Primary Examiner—David B. Springer
Attorney, Agent, or Firm—Oblon, Spivak, McClelland, Maier & Neustadt

[57] ABSTRACT

A process for the preparation of purified indigo comprises extracting the aqueous alkaline indoxylate solution arising from the synthesis with an inert water-insoluble solvent in the absence of oxygen before oxidizing the indoxylate solution to give indigo.

4 Claims, No Drawings

PURIFICATION OF INDIGO

Indigo is the largest-volume synthetic textile dye worldwide. Despite well-established production processes, it still contains impurities, for example up to 0.6% by weight of aniline and 0.4% by weight of N-methylaniline, and furthermore smaller amounts of other undesired compounds.

It is an object of the present invention to develop an effective and economical process for the purification of indigo in which the dye obtained is free or at least very substantially free from aromatic amines and other impurities.

Attempts to remove aromatic amines from indigo by known processes, for example by washing or by stirring with dilute acids, by steam distillation or by extraction with organic solvents, have hitherto not been successful, even if the dye is very finely ground.

Since these purification processes do not achieve any reduction in the concentration of aniline and N-methylaniline, even after intensive grinding of the dye, it must be assumed that these impurities are firmly included in the indigo crystal structure.

In all known industrial processes for the preparation of indigo, this dye is obtained in a final synthesis step by atmospheric oxidation of an aqueous alkaline indoxylate solution:

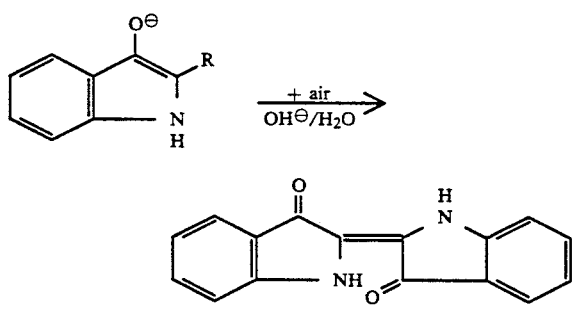

We have found that the abovementioned object is achieved by a process which gives very substantially purified indigo in good yield by extracting the aqueous alkaline indoxylate solution arising from the synthesis with a water-insoluble organic solvent in the absence of oxygen before oxidizing the indoxylate solution to give indigo.

After the phases have been separated, the extracted indoxylate solution can then be oxidized in a known manner to give indigo.

In order to ensure highly quantitative removal of the extractable impurities from the indoxylate solution, it is very important to carry out the extraction with the organic solvent in the strict absence of oxygen, which is advantageously achieved by working under nitrogen.

This is because even extremely small amounts of oxygen react with the dissolved indoxylate to form indigo, which then irreversibly includes aniline and N-methylaniline and other undesired impurities.

In order to prevent the formation, known from the literature, of Indoxyl Red (I), which proceeds by self-condensation of indoxylate and reduces the quality and yield of indigo, the extraction with the organic solvent is expediently carried out at from 55° C. to 75° C., preferably at approximately 65° C.

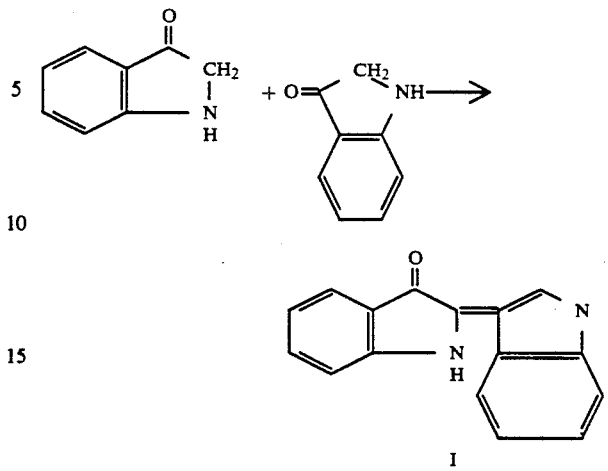

It has been shown that optimum extraction of the impurities present in the indoxylate solution can be achieved using an indoxylate solution : organic solvent ratio by weight (phase ratio) of from 1 : 0.1 to 1 : 1, preferably from 1 : 0.2 to 1 : 0.6.

In an advantageous embodiment of the process according to the invention, the aqueous alkaline indoxylate solution at 85° C. which is obtained during the preparation of indigo is immediately blanketed with nitrogen, cooled as rapidly as possible (in from about 5 to 15 minutes) to 65° C. and then extracted at 65° C. with the inert organic solvent in the phase ratio 1 : 0.5 for from 5 to 10 minutes. After the phases have been separated, the extracted indoxylate solution is oxidized in the conventional manner using air to give indigo having a purity of from 96% to 97%.

The aniline content of the dye is then from 0.02 to 0.04% by weight and the N-methylaniline content is <0.01% by weight.

By repeating the extraction operation and/or by increasing the amount of solvent used for the extraction, the content of aromatic amines in the indigo can be further reduced.

The solvent employed for the extraction, which contains the extractable impurities, is redistilled and then re-used for extraction.

The process can be carried out batchwise or continuously.

Examples of suitable solvents are hydrocarbons or chlorinated hydrocarbons, such as dichloroethylene, chlorobenzene, chloroform or xylenes, in particular toluene.

EXAMPLE 1

1,000 parts of an indoxylate solution at 85° C. obtained during the synthesis of indigo and containing 3.8% of indoxyl are cooled to 65° C. in 5 minutes under a nitrogen atmosphere in a 2 l stirred flask. 400 parts of toluene at 65° C. are added to the indoxylate solution, and the mixture is stirred vigorously at a stirrer speed of 500 rpm for 15 minutes under a constant $N_2$ atmosphere. The toluene phase is separated off, and the extracted indoxylate solution is converted into indigo in a conventional manner by passing air into the solution at from 65° C. to 75° C. The indigo is filtered off, washed until neutral and dried.

The purity of the dye obtained in this way is from 96% to 97% (measured photometrically). The indigo also contains from 0.02% to 0.4% of aniline and from 0.004% to 0.006% of N-methylaniline.

EXAMPLE 2

The process is carried out as in Example 1, but 250 parts of toluene are employed for extracting the indoxylate solution.

The indigo obtained contains from 0.04% to 0.06% of aniline and 0.01% of N-methylaniline.

EXAMPLE 3

The procedure is as in Example 2, but the extraction of the indoxylate solution is repeated after the phase separation with 250 parts of toluene. The indigo obtained contains from 0.02% to 0.04% of aniline and from 0.004% to 0.006% of N-methylaniline.

After the extraction of the indoxylate solution has been repeated a number of times with 250 parts of toluene, the indigo contains from 0.005% to 0.01% of aniline. N-methylaniline is no longer detectable.

We claim:

1. A process for the preparation of purified indigo, which comprises extracting the aqueous alkaline indoxylate solution arising from the synthesis with an inert water-insoluble solvent in the absence of oxygen before oxidizing the indoxylate solution to give indigo.

2. A process as claimed in claim 1, wherein the extraction of the indoxylate solution is carried out at from 55° C. to 75° C., preferably at 65° C.

3. A process as claimed in claim 1, wherein the extraction is carried out using an indoxylate solution : solvent ratio by weight of from 1 : 0.1 to 1 : 1, preferably from 1 : 0.2 to 1 : 0.6.

4. A process as claimed in claim 1, wherein the solvent used is toluene.

* * * * *